United States Patent [19]

Yardley et al.

[11] 4,272,432

[45] Jun. 9, 1981

[54] CLAUDOGENIC-INTERCEPTIVE NONAPEPTIDE

[75] Inventors: John P. Yardley; Alan Corbin, both of King of Prussia, Pa.

[73] Assignee: American Home Products Corporation, New York, N.Y.

[21] Appl. No.: 523,302

[22] Filed: Nov. 13, 1974

[51] Int. Cl.³ ............................................ C07C 103/52
[52] U.S. Cl. ..................... 260/112.5 R; 260/112.5 LH
[58] Field of Search ................ 260/112.5 R, 112.5 LH

[56] References Cited

PUBLICATIONS

Fujino et al: Biochem. Biophys. Res. Comm., 57, 1248–1256 (1974).
Coy et al: Biochem. Biophys. Res. Comm., 57, 335–340 (1974).

*Primary Examiner*—Delbert R. Phillips
*Attorney, Agent, or Firm*—Richard K. Jackson

[57] ABSTRACT

The invention embraces the novel nonapeptide L-pyroglutamyl-L-histidyl-L-tryptophyl-L-seryl-L-tyrosyl-D-alanyl-L-leucyl-L-arginyl-L-prolinethylamide, intermediates for its production and its use as a claudogenic-interceptive agent.

3 Claims, No Drawings

CLAUDOGENIC-INTERCEPTIVE NONAPEPTIDE

DESCRIPTION OF THE INVENTION

In accordance with this invention there is provided a novel nonapeptide of the formula:

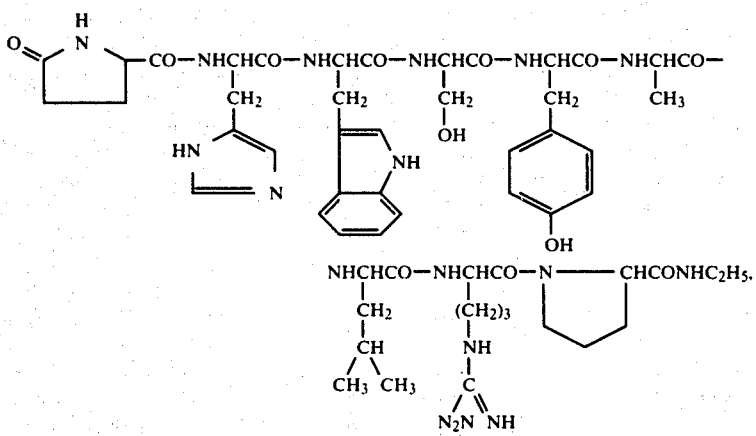

intermediates for its production and a method for its use as a claudogenic-interceptive agent useful for preventing gravidity in mammals.

The novel intermediates used for the production of the nonapeptide of this invention present the structural formula:

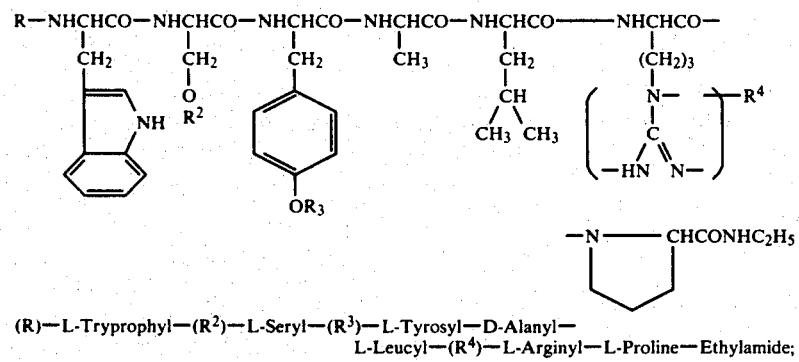

(R)—L-Tryprophyl—(R²)—L-Seryl—(R³)—L-Tyrosyl—D-Alanyl—L-Leucyl—(R⁴)—L-Arginyl—L-Proline—Ethylamide;

in which

R is —H or an α-amino protecting group which is not removed under coupling conditions while being capable of selective removal in the presence of protective groups in other functional sites of the polypeptide;

R² is hydrogen or an aliphatic hydroxyl protective group which is capable of selective removal in the presence of other protective groups while remaining intact during coupling reactions;

R³ is hydrogen or a phenolic hydroxyl protective group which remains intact during coupling reactions or deprotection of an α-amino group or carboxyl group while being capable of selective removal;

R⁴ represents the missing hydrogen atoms of the guanyl moiety of arginine or a protective group involving either one or two of the guanyl nitrogen atoms, capable of selective removal while remaining intact during coupling reactions and deprotection of other functional group in the molecule.

The other novel intermediates of this invention present the structural formula:

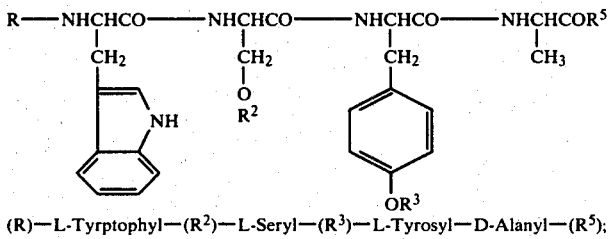

(R)—L-Tyrptophyl—(R²)—L-Seryl—(R³)—L-Tyrosyl—D-Alanyl—(R⁵);

in which the protecting groups R, R² and R³ are defined above, and

R⁵ is hydrazino or a carboxyl protecting group capable of selective removal while remaining intact during peptide coupling and deprotection of other functional groups.

The anti-gravidity agent of this invention, when administered to a female mammal, post-coitally pursuant to a daily regimen of at least about 300 micrograms per day per kilogram host body weight for a period in excess of three days, completely prevents pregnancy.

Although applicants do not wish to be bound by any specific theory of activity, they propose and believe, based upon studies conducted with a variety of animal models, that the nonapeptide of this invention exerts a claudogenic/interceptive action via stimulation of the hypophysial-ovarian steriod-uterine axis and/or a direct stimulation of the uterus itself as an extra-pituitary effect.

Applicants theory is predicated upon uterine weight changes induced by administration of the nonapeptide of this invention to intact animals, hypophysectomized animals and ovariectomized animals, which changes were comparable in all of the models. Thus, in the absence of the pituitary and in the absence of ovaries, a uterine weight change resulted upon administration of the nonapeptide of this invention, which change was directly correlatable with the weight change induced in normal animals. Hence, direct stimulation of the uterus is the plausible conclusion to be derived from these observations, as opposed to any essential interplay of the hypothalamus and pituitary.

In any event, regardless of the physiological pathway to the end result, the nonapeptide of this invention effectively prevents pregnancy in female mammals upon administration after coitus.

Hence the nonapeptide of this invention is useful as a "morning-after" contraceptive to prevent or terminate pregnancy in the female mammal. Within this context, the nonapeptide may be used as an anti-littering agent for control of rodent populations without use of rodenticides and their possible undesirable effect on other animals in the environment.

Pregnancy was avoided in the animal models by daily administration of the nonapeptide of this invention during the day 1 to day 3 period after coitus as well as upon daily administration over the day 1 to day 7 period and day 7 to day 12 period, post-coitus. Thus both a claudogenic (pre-implantation) as well as an interceptive (post-implantation) type of interference with pregnancy was established.

The procedure followed in evaluating the anti-gravidity properties of the nonapeptide of this invention was as follows: Mature, female, Sprague-Dawley rats (350±30 grams body weight) were caged with fertile male rats on the evening of proestrus. The presence of vaginal sperm the next morning was considered day 1 of pregnancy. The nonapeptide of this invention was administered subcutaneously in a corn oil vehicle on days 1-3, 1-7, or 7-12 of pregnancy. One-half the daily dose was administered at 9 A.M. and at 3 P.M. each day. The recipients of day 1-3 and 1-7 treatment were autopsied on day 14. The recipients of day 7-12 treatment were autopsied on day 18 of pregnancy. The effectiveness of the compound and its effective dose was established by the absence of uterine implantation sites and fetuses. The presence of at least one normal fetus was considered to be the criterion of pregnancy. The claudogenic/interceptive activity of the nonapeptide of this invention was thereby established at a daily dose of about 300 micrograms per kilogram host body weight.

For the purpose of defining the post-coital stages of pregnancy in the rat as an experimental model, the following schedule is provided in definition of post-coital contraceptive activity which, for the purpose of this disclosure, is intended to embrace both pre-(claudogenic) and post-(interceptive) implantation contraceptive activity: day 1—vaginal sperm; days 1-3—ova transport in oviducts, fertilization; days 3-5—blastocyst free in uterine lumen; days 5-7—implantation into uterine wall; days>7—post implantation.

Based upon the findings of activity in the prevention of development of pregnancy in the rat model and the fact that present evidence indicates that the hormonal situation relating to the reproductive cycle up to and including ovulation, is basically the same in all female vertebrates, e.g. the human reproductive cycle is physiologically analogous with that of the rat, the activity of the nonapeptide of this invention effectively interferes with the development of the blastocyst pre-and post-implantation in the uterus in all mammals, including the human.

Thus, in accordance with the use aspect of this invention there is provided a method for terminating pregnancy in a mammal which comprises administering L-pyroglutamyl-L-histidyl-L-tryptophyl-L-seryl-L-tyrosyl-D-alanyl-L-leucyl-L-arginyl-L-prolinethylamide to said mammal, post-coitally, in a daily regimen containing at least about 300 micrograms per kilogram host body weight for a period sufficient to terminate said pregnancy. In operation, the anti-gravidity compound of this invention interferes with the mechanism of gestation, whether that interference is as an early post-coital, pre-implantation contraceptive or as a post-implantation interceptive agent. Hence, the effective sequence of daily administration in the human is from day 1 of ovulation-fertilization to about day 6 to produce a claudogenic response, or from day 6 to about day 14 post ovulation—fertilization to effect an interceptive response in the gestational period. The human dose, based upon the posology of the experimental model, is approximately 14 milligrams per day for a fifty kilogram female.

The nonapeptide of this invention may be administered parenterally or orally in any convenient form, with or without conventional liquid or solid pharmaceutical adjuvants well known to the art. In addition, conventional adducts of the nonapeptide may be employed to prolong its effectiveness, such as the protamine zinc or aluminum adducts which are prepared by conventional techniques. Assimilation of the nonapeptide upon oral administration may be improved, if desired, by supplying an enteric coating, etc.

The nonapeptide of this invention may be prepared by solid phase synthesis or by solution methods. Examples 1-17 illustrate a solution preparation proceeding through (1) the preparation of Trp-Ser-Tyr-D-Ala-N$_2$H$_3$ in Examples 1-6; (2) the preparation of Leu-Arg-Pro-NHEt in Examples 7-12; (3) the coupling and deprotection of the tetrapeptide of Example 6 with the tripeptide of Example 12 and deprotection of the product in Examples 13 and 14; with (4) a final coupling of the heptapeptide of Example 14 with Glu-His-N$_2$H$_3$, as prepared in Examples 15 and 16, in Example 17.

Examples 18 through 22 illustrate the solid phase synthesis of the nonapeptide of this invention.

The reaction scheme followed in Examples 1-17 may be diagramed as follows, in which MA refers to mixed anhydride coupling; BOC is t-butyloxycarbonyl, Bzl is benzyl, Z is benzyloxycarbonyl and TFA is trifluoroacetic acid.

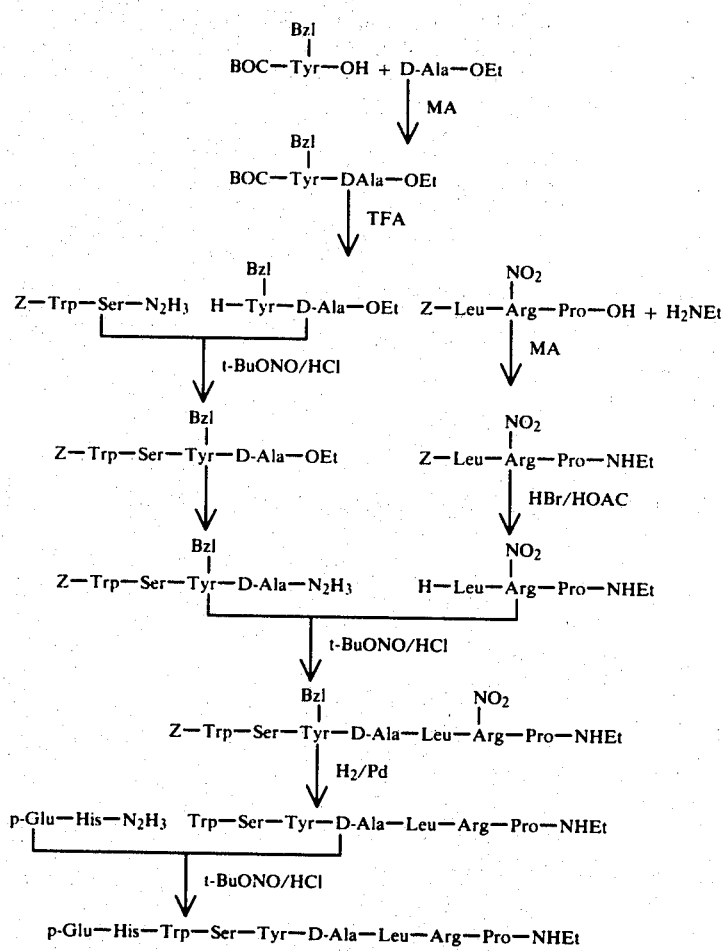

Although specific protecting groups are employed above and in the working examples, infra, it is to be understood, and it is well within the knowledge of the art skilled, that equivalent protecting groups may be employed without altering the overall reaction sequence.

Thus, the α-amino protecting groups applicable in the coupling sequence followed, are those which are not split-off during coupling conditions but are readily removed selectively in relation to other protecting groups in the molecule under conditions which otherwise do not effect the formed molecule. The preferred α-amino protecting groups include tert-butyloxycarbonyl, trityl, phthalyl, tosyl, allyloxycarbonyl, cyclopentyloxycarbonyl, tert-amyloxycarbonyl, benzloxycarbonyl, o or p-nitrobenzyloxycarbonyl and the like.

Carboxyl protecting groups must be stable during deprotection of α-amino groups, and include simple lower alkyl esters containing from 1 to 6 carbon atoms in the alcohol moiety as well as benzyl and substituted benzyl esters (in which o and/or p-substituents include the lower alkoxy, lower alkyl and nitro groups) and the like.

The hydroxyl groups of serine and tyrosine may be protected effectively by the acetyl, tosyl, benzoyl, tert-butyl, trityl, benzyl or benzyloxycarbonyl groups, the benzyl group being preferred.

The guanyl group of arginine is readily protected by nitro, tosyl, benzyloxycarbonyl, adamantyloxycarbonyl, trityl and similar groups; the first two mentioned protecting groups operating via control of the $N^\omega$ or $N^{\omega 1}$ nitrogen atoms while the latter mentioned groups control the $N^\delta$ nitrogen atom and either of the $N^\omega$ or $N^{\omega 1}$ atoms.

EXAMPLE 1

N-tert-Butyloxycarbonyl-O-benzyl-L-tyrosyl-D-alanyl ethyl ester

N-tert-Butyloxycarbonyl-O-benzyl-L-tyrosine (37.5 g., 0.1 mole) was dissolved in tetrahydrofuran (200 ml.), cooled to −15° C. and N-methylmorpholine (11 ml., 0.1 mole) added followed by isobutylchloroformate (13.4 ml., 0.1 mole). The reaction mixture was stirred for 5 minutes, then a solution of D-alanine ethyl ester hydrochloride (15.4 g., 0.1 mole) and N-methylmorpholine (11 ml., 0.1 mole) in dimethylformamide (100 ml.) was added and the mixture allowed to reach room temperature overnight.

The solvent was evaporated and the residue in ethyl acetate-n-butanol-chloroform washed with 5% $KHSO_4$, brine, saturated $NaHCO_3$ solution, brine. The organic phase was dried ($Na_2SO_4$), filtered and concentrated under reduced pressure until crystallization became rapid. After separation of product (32 g.) the mother liquors were evaporated and the residue crystallized from ethyl acetate-hexane to give a further 10 g. product for a total yield of 42 g. (89%), m.p. 129°–131° C.

An analytical sample was obtained by recrystallization of 1 g. of from ethyl acetate-hexane, m.p. unchanged.

Elemental Analysis for $C_{26}H_{34}N_2O_6$(470.55) Calc'd: C, 66.36; H, 7.28; N, 5.95. Found: C, 66.62; H, 7.35; N, 5.93.

EXAMPLE 2

O-Benzyl-L-tyrosyl-D-alanyl ethyl ester trifluoroacetate

N-tert-Butyloxycarbonyl-O-benzyl-L-tyrosyl-D-alanyl ethyl ester (19.5 g.) was dissolved in trifluoroacetic acid (200 ml.). The stirred solution was kept at 0° C. during 10 minutes then for 50 minutes at room temperature after which time the excess trifluoroacetic acid was removed under reduced pressure and at 25° C. The residue was evaporated from diethyl ether twice and finally precipitated from the ether solution with hexane. Yield approximately quantitative. Thin-layer chromatography indicated no starting material remained.

EXAMPLE 3

N-Benzyloxycarbonyl-L-tryptophyl-L-serine methyl ester

N-Benzyloxycarbonyl-L-tryptophan (24.5 g., 0.0725 mole) is dissolved in dimethylformamide (200 ml) and mixed with L-serine methyl ester hydrochloride (11.25 g., 0.073 mole) followed by dicyclohexylcarbodiimide (14.9 g., 0.073 mole). The reaction mixture is stirred for 1 hour at −10° C. then at room temperature overnight. The dicyclohexylurea which separates is filtered off and the filtrate is evaporated to dryness. The residue is taken in ethylacetate, washed with 5% aq. $KHSO_4$, water; sat. aq. $NaHCO_3$, water, dried over sodium sulfate. Evaporation to dryness affords a foam which on trituration with ethyl acetate crystallizes to give the above-titled dipeptide ester. In another preparation the residue is crystallized from ethyl acetate-pentane, 26.8 g. (85%) m.p. 140°–141° C.; $R_f$(Chloroform-methanol 10:1) 0.55; single spot with $I_2$ reagent.

EXAMPLE 4

N-Benzyloxycarbonyl-L-tryptophyl-L-seryl hydrazide

N-Benzyloxycarbonyl-L-tryptophyl-L-serine methyl ester of Example 3 (43.9 g., 0.1 mole) is dissolved in dimethylformamide (200 ml) and methanol (400 ml) and treated with hydrazine hydrate (85 ml) overnight. Most of the methanol is removed in vacuo and the residue is treated with 1.5 volumes water to afford the above-titled crystalline compound 39 g. (89%) m.p. 187°–188° C.; $R_f$ (Chloroform-methanol 10:1) 0.00; $R_f$(n-Butanol-water-acetic acid 4:1:1) 0.75; $R_f$(n-Butanol-water-acetic acid-pyridine 30:24:6:20) 0.70; $R_f$(n-Butanol-water-pyridine 3:1.5:2) 0.75; single spot with $I_2$ and Erlich reagents.

EXAMPLE 5

N-Benzyloxycarbonyl-L-tryptophyl-L-seryl-O-benzyl-L-tyrosyl-D-alanyl ethyl ester N-Benzyloxycarbonyl-L-tryptophyl-L-seryl hydrazide (19 g., 4.3×10$^{-2}$ mole) was dissolved in dimethylformamide (180 ml.) and treated at −30° C. with 3.9 N HCl/tetrahydrofuran (34 ml., 1.34×10$^{-1}$ mole). tert-Butylnitrite (6.1 ml., 5.2×10$^{-2}$ mole) was added and the solution stirred at −25° C. during 20 minutes, then triethylamine (29 ml., 2.12×10$^{-1}$ moles) was added followed immediately by a solution of o-benzyl-L-tyrosyl-D-alanyl ethyl ester trifluoroacetate (oily solid, 4.2×10$^{-2}$ mole) in dimethylformamide (80 ml.). The pH of the solution at this time was about 8. After stirring at −25° C. during 2 hours the reaction mixture was stored at 5° C. during two days after which time the reaction mixture was filtered and evaporated. The residue on attempted distribution between ethyl acetate-butanol (1:1) and $KHSO_4$ forms a solid at the interface. The solid was separated and washed with water, saturated $NaHCO_3$, water and dried to give 19.5 g. product (58% yield). $R_f$($CHCl_3$: methanol 10:1; silicagel) 0.70. Amino acid analysis: Trp (0.72), Ser (1.05), Tyr (0.92), Ala (1.0).

EXAMPLE 6

N-Benzyloxycarbonyl-L-tryptophyl-L-seryl-O-benzyl-L-tyrosyl-D-alanyl hydrazide

N-Benzyloxycarbonyl-L-tryptophyl-L-seryl-O-benzyl-L-tyrosyl-D-alanyl ethyl ester (10.5 g., 1.35×10$^{-2}$ mole) in methanol (400 ml.) dimethyl-formamide (150 ml.) was treated with hydrazine hydrate (20.5 ml., 85%) at room temperature overnight. Methanol was removed in vacuo and the concentrate diluted with water. The precipitate was removed by filtration, washed thoroughly with cold methanol, and dried to give 8.5 g. product (83% yield). Thin-layer chromatography indicated no starting material remained.

EXAMPLE 7

N-Benzyloxycarbonyl-N$^g$-nitro-L-arginyl-L-proline methyl ester

N-Benzyloxycarbonyl-N$^g$-nitro-L-arginine (35.5 g., 0.1 mole) is dissolved in 10% dimethylformamide in dichloromethane (ca. 150 ml) and cooled to −15° C., then N-methyl-morpholine (11.1 ml., 0.1 mole) is added followed by isobutylchloroformate (13.4 ml, 0.1 mole) while the mixture was kept cold. After 5 minutes a cold solution of L-proline methyl ester hydrochloride (16.5., 0.1 mole) and triethylamine (13.6 ml, 0.1 mole) in dimethylformamide is added. The temperature is brought to 0° C. and maintained there for 1 hour, then allowed to rise to room temperature and remain there for 18 hours.

The mixture is filtered and the filtrate concentrated under reduced pressure at 30° C. The residue is taken up in 1:1 ethyl acetate/n-butanol and washed with 5% $KHSO_4$, water, aq. $NaHCO_3$, brine. The organic phase is dried over $Na_2SO_4$, filtered and concentrated in vacuo until a solid starts to precipitate. The solution is cooled to 0° C. and left for 18 hours, then the crystalline compound which separated is filtered. Yield 16.3 g. (35%) of the above titled product.

On further concentration of the mother liquor a second crop was obtained 18.7 g. (40%) mp 154°–156° C.; $[\alpha]_D^{25}$ −46.7 (c 0.5%, methanol); $R_f$(Chloroform-methanol 9:1) 0.6.

EXAMPLE 8

N$^g$-Nitro-L-arginyl-L-proline methyl ester, hydrobromide

N-Benzyloxycarbonyl-N$^g$-nitro-L-arginyl-L-proline methyl ester (16.3 g., 35.1 mmoles) is treated with 30% hydrobromic acid in glacial acetic acid (50 ml) for one hour and at room temperature. Dry diethyl ether (ca. 500 ml) is added to give a pale yellow very hygroscopic solid. The product is not characterized further due to the very hygroscopic nature. It is dried in vacuo over KOH and used for the next reaction.

EXAMPLE 9

N-Benzyloxycarbonyl-L-leucyl-N$^g$-nitro-L-arginyl-L-proline methyl ester

N-Benzyloxycarbonyl-L-leucine (8.84 g., 33.4 mmoles) is dissolved in tetrahydrofuran (100 ml) and cooled to 15° C. N-methylmorpholine (3.73 ml, 33.3 mmoles) is added, followed by isobutylchloroformate (4.36 ml, 33.3 mmoles). After five minutes at −15° C., a solution of N$^g$-nitro-L-arginyl-L-proline methyl ester hydrobromide in dimethylformamide is added and the solution PH adjusted to 7.5 with triethylamine, is added (during the neutralization the solution is kept at 0° C.). The reaction mixture is kept at 0° C. for one hour, then allowed to rise to room temperature slowly and remain there for 18 hours after which time the solvent is removed in vacuo and at 30° C. The residue is taken up in ethyl acetate/n-butanol, 2:1, and washed with 5% KHSO$_4$, water, aq. KHCO$_3$, brine. The organic phase is dried over sodium sulfate, filtered and concentrated under reduced pressure at 30° C. The resulting gum is taken up in ethyl acetate and precipitated with diethyl ether. A white solid of the above-identified product is obtained, 13.11 g. (68%). m.p. 93°–96° C.; $[\alpha]_D^{25}$ −50.46 (c 0.34%, Methanol); R$_f$(Chlorform-methanol 9:1)0.70.

EXAMPLE 10

N-Benzyloxycarbonyl-L-leucyl-N$^g$-nitro-L-arginyl-L-proline

N-Benzyloxycarbonyl-L-leucyl-N$^g$-nitro-L-arginyl-L-proline methyl ester (13 g., 23 mmoles) is dissolved in 1:1 dioxane/N-sodium hydroxide (50 ml) and stirred for 2 hours at room temperature. Thin layer chromatography shows no starting material present. The solution is adjusted to pH 6.5 with 1.5 N-hydrochloric acid and concentrated in vacuo at 30° C. to a small volume. The residue is diluted with water (ca. 200 ml) and cooled to 0° C., then acidified to pH 3 with 1.5 N hydrochloric acid. The while solid which crystallizes out is collected and washed with cold water 11.8 g. (92%); $[\alpha]_D^{25}$ −54.84 (c 1%, methanol); R$_f$ (n-Butanol-water-acetic acid-pyridine 30:24:6:20) 0.70.

EXAMPLE 11

N-Benzyloxycarbonyl-L-leucyl-N$^g$-nitro-L-arginyl-L-proline-N-ethylamide

N-Benzyloxycarbonyl-L-leucyl-N$^g$-nitro-L-arginyl-L-proline (16.91 g., 30 m moles) in tetrahydrofuran (150 ml.) was cooled to −15° C., then N-methylmorpholine (3.33 ml., 30 mmoles) was added, followed by isobutylchloroformate (4.02 ml., 30 mmoles). After 5 minutes at −15° C. ethylamine (2 ml., 31 mmoles) was added. After 1 hour at 0° C. the reaction mixture was allowed to attain room temperature overnight.

The reaction mixture was filtered and concentrated in vacuo at 30° C. The residue was taken up in ethyl acetate-N-butanol (1:1) and washed with 5% KHSO$_4$, water, saturated NaHCO$_3$, brine and dried (Na$_2$SO$_4$). Evaporation of the organic phase under reduced pressure at 25°–30° C. afforded a gum which was taken up in ethanol, filtered, and reprecipitated on addition of diethyl ether to give the product.

EXAMPLE 12

L-leucyl-N$^g$-nitro-L-arginyl-L-proline-N-ethylamide hydrobromide

N-Benzyloxycarbonyl-L-leucyl-N$^g$-nitro-L-arginyl-L-proline-N-ethylamide (6.0 g., 10 mmole) was treated with anhydrous 30% HBr/glacial acetic acid for 5 minutes in an ice bath then for one hour at room temperature. Addition of diethyl ether initially afforded a gummy solid which on trituration afforded a pale tan, hygroscopic solid which was filtered, washed with diethyl ether and used directly in the preparation of N-benzyloxycarbonyl-L-tryptophyl-L-seryl-O-benzyl-L-tryosyl-D-alanyl-L-leucyl-N$^g$-nitro-L-arginyl-L-proline-N-ethylamide.

EXAMPLE 13

N-Benzyloxycarbonyl-L-tryptophyl-L-seryl-O-benzyl-L-tyrosyl-D-alanyl-L-leucyl-N$^g$-nitro-L-arginyl-L-proline-N-ethylamide N-Benzyloxycarbonyl-L-tryptophyl-L-seryl-O-benzyl-L-tyrosyl-D-alanyl hydrazide from Example 6 (6.0 g., 8 mmoles) in dimethylformamide (100 ml.), cooled to −20° C., was treated with 3.75 N-HCl/tetrahydrofuran (6.4 ml., 24 mmoles) followed by tert-butyl nitrite (1.3 ml., 1.12 mmoles). After 20 minutes at −20° C., the reaction mixture was treated with triethylamine (4.5 ml., 32 mmoles) followed by a dimethylformamide (30 ml.) solution of L-leucyl-N$^g$-nitro-L-arginyl-L-proline-N-ethylamide hydrobromide (total product Example 12) pretreated at −20° C. with triethylamine to pH 7.5. After stirring 1½ hour at −20° C. the mixture was evaporated in vacuo at or below 35° C. and the residue triturated with water. The solid precipitate was filtered and washed thoroughly with 1 N HCl, H$_2$O and dried to 9.1 g. product. Reprecipitation from methanol with diethyl ether afforded 7.0 g., R$_f$ (n-butanol; acetic acid; water 4:1:5 upper phase; silicagel) 0.66.

EXAMPLE 14

L-Tryptophyl-L-seryl-L-tyrosyl-D-alanyl-L-leucyl-L-arginyl-L-proline-N-ethylamide diacetate N-Benzyloxycarbonyl-L-tryptophyl-L-seryl-O-benzyl-L-tyrosyl-D-alanyl-L-leucyl-L-arginyl-L-proline-N-ethylamide (2.0 g.) in methanol, acetic acid, water (1:1:1, 100 ml.) was shaken in an atmosphere of hydrogen with a 5% Pd on charcoal catalyst (600 mg.) during 20 hours. The catalyst was removed by filtration and the filtrate evaporated. The residue in ethanol was evaporated twice and finally precipitated with diethyl ether from a small volume of ethanol to give the product (1.55 g.). R$_f$(n-butanol; acetic acid; water 4:1:5; silica gel) 0.24. $[\alpha]_D^{25}$−26.7 (c, 1.013, 1% HOAc).

Amino acid analysis: Trp (0.83), Ser (0.82), Tyr (0.99), Ala (1.0), Leu (0.96), Arg-not significant due to overlap with EtNH$_2$ peak, Pro (1.0) ninhydrin, Sakaguchi and Ehrlich tests positive.

EXAMPLE 15

L-(5-Oxoprolyl)-L-histidine methyl ester

L-5-Oxoproline (13 g., 0.1 mole) and L-histidine methyl ester dihydrochloride (22.8 g., 0.1 mole) are suspended in dimethylformamide (200 ml). The mixture is treated with triethylamine (27 ml, 0.2 moles) and cooled at −5° C., then dicyclohexylcarbodiimide (20.6 g., 0.1 mole) is added and the mixture is stirred for 2 hours at −5° C. and overnight at room temperature. The dicyclohexylurea which separates is filtered off and the filtrate is evaporated to dryness. The residue is triturated with water and the insoluble solid is filtered off. The filtrate is evaporated to dryness and the residue dried twice with abs. ethanol. The oily residue crystallizes from abs. EtOH to afford the above titled dipeptide methyl ester 13 g (45%), m.p. 198°–199° C.; $[\alpha]_D^{22}$ −4.3 (c 1.0%, Methanol); $R_f$(n-Butanol-water-acetic acid 4:1:1) 0.30; $R_f$(n-Butanol-water-acetic acid-pyridine 30:24:6:20) 0.50; single spot with Pauly and $I_2$ reagents.

Elemental Analysis for $C_{12}H_{16}N_4O_4$ (280.28) Calc'd: C, 51.42, H, 5.75, N, 19.99. Found: C, 51.34, H, 6.04, N, 20.12.

EXAMPLE 16

L-(5-Oxoprolyl)-L-histidyl hydrazide

L-(5-Oxoprolyl)-L-histidine methyl ester (10 g. 0.036 mole) is dissolved in methanol (150 ml) and treated with hydrazine hydrate 99% (8 ml) at −10° C. for one hour then at room temperature overnight. The white solid which separates is filtered and washed with methanol and then with diethyl ether. Recrystallization from water-ethanol affords the above-titled dipeptide hydrazide 8.8 g. (88%-Recrystallization from water-ethanol [78%] m.p. 241.5°–242° C.; $[\alpha]_D^{22}$ −14.50 (c 1.0%, $H_2O$); $R_f$(n-Butanol-water-acetic acid 4:1:1) 0.05; $R_f$(n-Butanol-water-acetic acid-pyridine 30:24:6:20) 0.10; single spot with Pauly and $I_2$ reagents.

EXAMPLE 17

L-(5-oxoprolyl)-L-histidyl-L-tryptophyl-L-seryl-L-tyrosyl-D-alanyl-L-leucyl-L-arginyl-L-proline-N-ethylamide diacetate L-(5-oxoprolyl)-L-histidyl hydrazide (840 mg., 3 mmoles) in dimethylformamide (18 ml.) was treated, at 26° C. with 3.6 N HCl/tetrahydrofuran (2.5 ml., 9 mmoles) followed by tert-butyl nitrite (0.46 ml., 4 mmoles). After stirring for 15 minutes, triethylamine (1.68 ml., 12 mmoles) was added followed by a cold solution of L-tryptophyl-L-seryl-L-tyrosyl-D-alanyl-L-leucyl-L-arginyl-L-proline-N-ethylamide diacetate (1.5 g., 1.43 mmoles) in dimethylformamide (10 ml.) containing triethylamine (0.36 ml., 2.6 mmoles). After stirring at −20° C. for 30 minutes, the reaction mixture was stored at 0° C. during 60 hours, after which time it was evaporated in vacuo at or below 35° C. and the residue lyophyllized from water. The peptide was purified in two stages. The first stage consisted of gel filtration on a column of Biogel P-2 (135×2.5 cm.) in 2 N acetic acid. Peptide material was located by Ehrlich spot test, ultra-violet (280 mm.) analysis and thin layer chromatography on silica; n-butanol:acetic acid: water (4:1:5 upper phase). $R_f$ 0.18. The second stage utilized partition chromatography on a column of Sephadex G-25 (91×2.6 cm), previously equilibrated with the lower phase followed by the upper phase of the N-butanol:acetic acid: water system mentioned above. Elution with upper phase afforded 180 mg. in fractions 60–72. The lyophyllate, still pale colored at this point, was given a final gel filtration through the column used in stage one to give 119 mg. title compound. Fraction size (6–7 ml.). $[\alpha]_D^{25}$ −40.7° (c 0.591% acetic acid). Hydrolysis of the peptide in 6 N HCl containing 4% thioglycollic acid for 20 hours at 110° C. in a closed system under nitrogen Ser (0.92), Glu (1.02), Pro (1.02), Ala (1.0), Leu (0.94), Tyr (1.01), His (1.03), Arg (not significant overlap with $EtNH_2$).

Thin layer chromatography n-butanol:acetic acid:water (4:1:5) upper phase $R_f$ 0.68 (cellulose plates) and n-butanol:ethyl acetate:acetic acid:water (1:1:1:1) $R_f$ 0.68 (silica gel).

EXAMPLE 18

Preparation of tert-butyloxycarbonylproline resin (method of Gisin, Chim. Acta, 56, 1476 [1973]

Tert-Butyloxycarbonylproline (5.8 g., 27 mmoles) in an ethanol (35 ml.)-water (15 ml.) mixture was treated with concentrated aqueous cesium hydrogen carbonate solution until the pH of the solution reached 7. The reaction mixture was stripped and dried by repeated stripping using ethanol, ethanol-benzene, benzene (three times). The foam residue was dried over phosphorous pentoxide, in vacuo at room temperature overnight.

The total product in dimethylformamide (275 ml.) was stirred overnight at 50° C., under nitrogen, with Bio-Beads S.X. 1 Resin (chloromethylated capacity 0.89 meq./g.). The filtered resin was washed thoroughly with dimethylformamide (twice), dimethylformamide-10% water (twice), dimethylformamide (twice), methanol (twice), chloroform (thrice) and dried over $P_2O_5$. Amino acid analysis indicated a substitution on the resin of 0.64 meq./g.

In a similar experiment using chloromethylated resin with a capacity of 0.69 meq./g. a substitution of 0.5 meq./g. was obtained.

EXAMPLE 19

L-Pyroglutamyl-$N^{im}$-tosyl-L-histidyl-L-tryptophyl-O-benzyl-L-seryl-O-(2,6-dichlorobenzyl)-L-tyrosyl-D-alanyl-L-leucyl-$N^g$-tosyl-L-arginyl-L-prolyl acyl resin ester

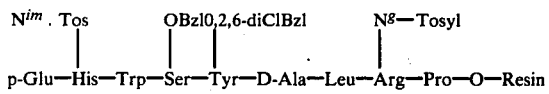

Tert-Butyloxycarbonyl-prolyl acyl resin ester (20 g.) in a Merrified vessel was treated to the following wash cycle (a) methylene chloride-trifluoroacetic acid prewash (5 minutes), (b) methylene chloride-trifluoroacetic acid (2×15 minutes), (c) methylene chloride (twice), (d) dimethylformamide, (e) dimethylformamide-12.5% triethylamine (2×10 minutes), (f) dimethylformamide, (g) methylene chloride (twice), (h) methanol (twice), (i) methylene chloride (thrice), allowing a contact time of at least 3 minutes each if not indicated otherwise.

The resin so prepared was gently shaken with tert-butyloxycarbonyl-$N^g$-tosyl arginine (25 meq.) in 1:1 methylene chloride-dimethylformamide during 5 minutes followed by the addition of 1 M dicyclohexylcarbodiimide (25 ml., 25 meq.) in two portions 30 minutes apart. Shaking was continued during 18 hours. The peptide resin was washed successively with (j) methanol, (k) methylene chloride, (l) methanol (twice), (m) methylene chloride (twice). Usually to test for completeness of reaction, the peptide-resin was subjected to a ninhydrin test following the procedure of E. Kaiser et al., Analytical Biochemistry 34, 595 (1970). Proline, however, is anomalous giving a weak color reaction in the above test so that coupling was repeated using 8.3 mmoles tert-butyloxycarbonyl-N-tosyl-arginine and 8.3 mmoles dicyclohexylcarbodiimide.

The following amino acid residues were introduced sequentially onto a washed (steps (j)-(m)), deprotected and neutralized, steps ((a)-(i)) peptide resin, tert-butyloxycarbonyl-L-leucine hydrate (25 meq.), tert-butyloxycarbonyl-D-alanine(25 meq.), tert-butyloxycarbonyl-O-(2,6-dichloro-benzyl)-L-tyrosine (25 meq.), tert-butyloxycarbonyl-O-benzyl-L-serine (25 meq.), tert-butyloxycarbonyl-L-tryptophan (25 meq.). All couplings were mediated using 25 meq. 1 M dicyclohexylcarbodiimide in methylene chloride as described for the addition of tert-butyloxycarbonyl-N$^g$-tosyl-arginine except for the case of tert-butyloxycarbonyl-L-leucine, the dicyclohexylcarbodiimide reagent being added first to reduce the possibility of peptide loss via diketo piperazine formation, cf. B. F. Gisin & R. B. Merrifield, J. Amer. Chem. Soc., 94, 3102 (1972). The remainder of the synthesis was carried out in a Beckmann 990 peptide synthesizer, using 8 g. of peptide resin and by modifying the above procedures by the addition of 5% (volume) of ethane-dithiol to the deprotection steps (a) and (b), by mediating couplings with a 10% excess of diisopropylcarbodiimide (0.5 molar) in methylene chloride and by the use of a shortened 5 hour coupling time. The following amino acids added were tert-butyloxycarbonyl N$^{im}$-tosyl-L-histidine (6 meq.+3 meq. recouple) and L-pyroglutamic acid (6 meq.). The resin was washed steps (j)-(m) and dried in vacuo to give the title compound.

EXAMPLE 20

L-pyroglutamyl-N$^{im}$-tosyl-L-histidyl-L-tryptophyl-O-benzyl-L-seryl-O-2,6-dichlorobenzyl-L-tyrosyl-D-alanyl-L-leucyl-N$^g$-tosyl-L-arginyl-L-prolin-ethylamide Protected peptide-resin (ca. 8.6 g.) from Example 19 and ethylamine (120 ml.) were stirred overnight in a glass pressure bottle. Ethylamine was removed under reduced pressure and the residue washed with methanol, dimethylformamide (four times), methanol and methylene chloride. The combined filtrates were evaporated in vacuo below 35° C. to give the title compound (2.6 g.).

EXAMPLE 21

L-pyroglutamyl-L-histidyl-L-tryptophyl-L-seryl-L-tyrosyl-D-alanyl-L-leucyl-L-arginyl-L-prolinethylamide The produce of Example 20 (2.6 g.) was treated in vacuo with anhydrous liquid hydrogen fluoride (120 ml.) and anisole (35 ml.) for 50 minutes at 0° C. Hydrogen fluoride was removed under reduced pressure and the residue distributed between diethyl ether and 10% aqueous acetic acid. Lyophyllization of the acid layer afforded the crude title produce (2.1 g.).

EXAMPLE 22

Purification and characterization of L-pyroglutamyl-L-histidyl-L-tryptophyl-L-seryl-L-tyrosyl-D-alanyl-L-leucyl-L-arginyl-L-prolinethylamide The crude peptide (2.1 g.) in a minimum volume of 2 N acetic acid was applied to a column of Sephadex G-15 fine previously equilibrated with 2 N acetic acid and then eluted with the same solvent. Fractions of 9 ml. each were collected. Peptide material was located by Ehrlich spot test and UV analysis. Two major fractions were obtained, I 29-32 (800 mg.); II 34-40 (1.0 g.). Fraction II had the appropriate amino-acid analysis and was rechromatographed on a partition column of Sephadex G-25 fine (2.6×90 cm.) prepared by equilibration with lower phase and then upper phase of the BAW system (n-butanol:acetic acid: water, 4:1:5). Elution with upper phase afforded fractions A 62-70 (180 mg.), B 71-80 (130 mg.), C 95-110 (120 mg.). Fractions A and B form a symmetrical peak and had similar amino acid analyses and thin layer chromatographic behavior on either silica gel or cellulose plates (Brinkmann). R$_f$(n-butanol:acetic acid:water 4:1:5), 0.18 silica gel); 0.68 (cellulose), R$_f$(n-butanol:ethyl acetate:acetic acid:water 1:1:1:1), 0.68 (silica gel). $[\alpha]_D^{22}$ −41.5 (c, 1.029 1% acetic acid.)

Hydrolysis of the peptide in 6 N HCl containing 4% thioglycollic acid for 20 hours at 110° C. in a closed system under nitrogen: Ser (0.88), Glu (0.96), Pro (1.14), Ala (1.0), Leu (1.11), Tyr (1.01), His (0.97), Trp (0.78), Arg (1.05).

What is claimed is:

1. A compound of the formula:

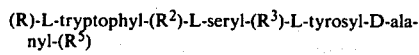

(R)-L-tryptophyl-(R$^2$)-L-seryl-(R$^3$)-L-tyrosyl-D-alanyl-(R$^5$)

in which

R is —H or an α-amino protecting group selected from the group consisting of tert-butyloxycarbonyl, trityl, phthalyl, tosyl, allyloxycarbonyl, cyclopentyloxycarbonyl, tert-amyloxycarbonyl, benzyloxycarbonyl, o-nitrobenzyloxycarbonyl and p-nitrobenzyloxycarbonyl;

R$^2$ and R$^3$ are independently —H or a hydroxyl protecting group selected from the group consisting of acetyl, tosyl, benzoyl, tert-butyl, trityl, benzyl and benzyloxycarbonyl; and, R$^5$ is hydrazino or a carboxyl protecting group selected from the group consisting of an alkyl ester containing from 1 to 6 carbon atoms in the alcohol moiety, benzyl ester or a substituted benzyl ester in which said substitution is in ortho and/or para position and is represented by lower alkyl, lower alkoxy or nitro group.

2. The compound of claim 1 which is benzyloxycarbonyl-L-tryptophyl-L-seryl-O-benzyl-L-tyrosyl-D-alanyl hydrazide.

3. The compound of claim 1 which is benzyloxycarbonyl-L-tryptophyl-L-seryl-O-benzyl-L-tyrosyl-D-alanyl ethyl ester.

* * * * *